US006242265B1

(12) United States Patent
Giesendorf

(10) Patent No.: US 6,242,265 B1
(45) Date of Patent: Jun. 5, 2001

(54) USE OF DOUBLY OR TRIPLY CHARGED CATIONS IN IMMUNOCHEMICAL ASSAYS

(75) Inventor: Bernhard Giesendorf, Dornburg-Frickhofen (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/246,569

(22) Filed: May 20, 1994

Related U.S. Application Data

(63) Continuation of application No. 08/016,210, filed on Jan. 21, 1993, now abandoned, which is a continuation of application No. 07/466,598, filed on Jan. 17, 1990, now abandoned.

(30) Foreign Application Priority Data

Jan. 19, 1989 (DE) .................................................. 39 01 458

(51) Int. Cl.[7] ........................ G01N 33/543; G01N 33/00; G01N 33/53; G01N 33/531
(52) U.S. Cl. ............................ 436/518; 422/56; 422/57; 422/68.1; 435/7.1; 435/7.92; 435/174; 435/805; 435/815; 435/961; 435/962; 435/967; 436/174; 436/175; 436/177; 436/528; 436/531; 436/547; 436/821; 436/825
(58) Field of Search ..................................... 436/174, 175, 436/177, 518, 528, 529, 530, 531, 543, 547, 810, 821, 825, 826, 827; 435/11, 805, 961, 962, 967, 970, 188, 7.1, 7.92, 174, 815; 422/56, 57, 68.1

(56) References Cited

U.S. PATENT DOCUMENTS

| 4,234,316 | * | 11/1980 | Hevey | 422/58 |
| 4,578,349 | * | 3/1986 | Schaffel | 436/177 |
| 4,618,486 | * | 10/1986 | Lundblad | 424/11 |
| 4,746,605 | * | 5/1988 | Kerscher et al. | 435/11 |
| 4,794,090 | * | 12/1988 | Parham et al. | 436/531 |
| 4,891,311 | * | 1/1990 | Anawis et al. | 435/7 |

FOREIGN PATENT DOCUMENTS

| 0152847 | | 2/1985 | (EP) . | |
| 155957 | * | 7/1986 | (JP) | 435/962 |

OTHER PUBLICATIONS

Nicolai–Scholten, et al. "The enzyme–linked immunosorbent assay (ELISA) for determination of IgG and IgM antibodies after infection with mumps virus," Med. Microbiol. Immunol., vol. 168, pp. 81–90, 1980.

Tijssen, Practice and Theory of Enzyme Immunoassays, pp. 314–328 (1985).*

Bangs, Uniform Latex Particles, pp. 51–58 (1984).*

Harlow, E. and Lane, D. Antibodies: A Laboratory Manual. 1988: Cold Spring Harbor Laboratory. pp. 553–612, Dec. 1988.*

* cited by examiner

Primary Examiner—Long V. Le
Assistant Examiner—Kartic Padmanabhan
(74) Attorney, Agent, or Firm—Finnegan, Henderson, Farabow, Garrett and Dunner, L.L.P.

(57) ABSTRACT

The use of calcium salts, magnesium salts or combination thereof in immunochemical methods for the determination of an analyte in a sample. These salts increase the specificity of such determinations, in particular, the background signal being reduced by addition of these salts in solid phase immunochemical methods.

5 Claims, No Drawings

USE OF DOUBLY OR TRIPLY CHARGED CATIONS IN IMMUNOCHEMICAL ASSAYS

This application is a continuation, of application Ser. No. 08/016,210, filed Jan. 21, 1993, now abandoned, which was a continuation of application Ser. No. 07/466,598, filed Jan. 17, 1990, abandoned.

The invention relates to the use of doubly or triply charged cations in methods for immunochemical detection and for the determination of an analyte in biological material.

Known immunochemical assay systems make use of added proteins, polysaccharides and/or surfactants which are not involved in the immunochemical reaction but which are suitable for having a beneficial effect on the result of a reaction of this type.

For solid-phase ELISAs, which represent a selection of assay systems of this type, the incubation media which are required (buffer solutions, incubation milieus) and which contain the analyte and are brought into contact with the solid phase must have a composition such that the non-specific binding of concomitant substances of the sample and/or of the conjugate to the solid phase is prevented. This is why the known additives such as proteins, for example albumin, IgG, casein, hydrolyzed gelatin and the derivatives thereof and mixtures of proteins or else human or animal sera, as well as surfactants, are used in the incubation media.

EP 0,152,847 describes enzyme-antigen and enzyme-antibody conjugates which contain calcium salts and polyoxyethylene together, where the stability of a conjugate in aqueous solution is increased by adding both substances but not by each of the substances alone. DE 3,638,767 describes an incubation medium for solid-phase immunochemical assays, for example an ELISA, which contains lactoferrin, fetal calf serum, polyoxyethylene 20 sorbitan monolaurate (Tween 20®) and buffer salts.

DE 3,807,478 mentions amine oxides as an advantageous addition for immunochemical agents, in particular for incubation media contained therein.

It has now been found, surprisingly, that doubly or triply charged cations are suitable for addition to agents with which an analyte in a sample is detected or determined by an immunochemical reaction, in particular in combination with the abovementioned additives, in order to have a beneficial effect on the immunochemical reaction, which increases the specificity of the detection and determination of the analyte.

Hence the invention relates to the use of doubly or triply charged cations, preferably of water-soluble magnesium and/or calcium salts, in a method for the immunochemical detection and for the immunochemical determination of an analyte contained in a biological material, wherein the appropriate salts are present in dissolved form in a concentration of 5 to 500 mmol/l when the analyte is brought into contact with an unlabeled reactant.

The water-soluble magnesium or calcium salts preferred from the group thereof are those whose anions do not interfere with the immunochemical reaction. Preferred anions are acetate, chloride and citrate, particularly preferably chloride.

Methods within the meaning of the invention are those in which precipitates are generated as dispersion or in a gel or agglutinates of particles, or whose absence is effected, or those in which the immunochemical reaction takes place on a solid phase.

The preferred methods are those called solid-phase immunochemical assays.

In this connection, a solid phase is a carrier which is insoluble in water and to which one or more reactants is bound. The analyte can either bind to a reactant or, if several reactants are present bound to the carrier, detach at least one of these by its own binding and release it into the aqueous phase.

Examples of carriers are latex particles, granular, swellable or non-swellable material, beads, inside surfaces of tubes, microassay plates as particular embodiment of an arrangement of tubes as well as porous materials to be termed an absorbent matrix.

In immunochemical methods, antigen and antibody are used both as analytes and as reactants as well as other bioaffinity binding partners for the reactants or else the analytes, for example lectins, complement, protein A or G as well as derivatized biotin and avidin.

The multiply charged cations can be contained in dry form in a device for receiving a sample, for example in a sample-receiving vessel or in a receiving zone, for example an absorbent matrix, for the sample on a socalled called "dry chemical" assay system; or else in an aqueous solution which also contains buffer salts and a detergent and, where appropriate, stabilizing additives such as proteins or polysaccharides as substances which likewise stabilize the analyte, the multiply charged cations being contained in a concentration of 5 to 500 mmol/l, preferably of 30 to 100 mmol/l, particularly preferably of 50 to 60 mmol/l.

Examples of the biological materials which contain the analyte, which are also called the sample, are tissue from biopsies or autopsies, blood cells, serum or plasma, secretions, CSF, blood from inflamed and non-inflamed tissue, the products of necrosis and metabolic excretions.

Preferred immunochemical methods are those in which one of the reactants is present in solid phase, in which case the sample is brought into contact with the solid phase in the presence of multiply charged cations, where appropriate together with other immunochemical reactants apart from those on the solid phase and reagents for detecting the analyte, whereupon the solid phase is separated from the liquid phase and either the analyte bound to the solid phase is determined or the unbound analyte is determined.

In the examples which follow, the advantages of the use of multiply charged cations in methods for the detection and for the determination of antibodies directed against the agents causing (1) infectious bovine rhinotracheitis (IBR) or infectious pustular vulvovaginitis (IPV) and (2) bovine leukosis are explained.

EXAMPLES

Example 1

ELISA for Detecting Antibodies Against the Agent Causing IBR and IPV 1.1 Buffer and Reagent Solutions The following buffer and reagent solutions were prepared:

1.1.1 PBS-Tween 20®

Phosphate-buffered physiological saline, pH 7.2 (PBS), i.e. 10 mmol/l $Na_2HPO_4/KH_2PO_4$, pH 7.2 in 140 mmol/l NaCl containing 10 g/l polyoxyethylene 20 sorbitan monolaurate (Tween 20®).

1.1.2 Sample Dilution Buffer (PT)

PBS containing 40 g/l Tween 20®.

1.1.3 Sample Dilution Buffer Containing 50 mmol/l $MgCl_2$ (PT-Mg)

10 g/l $MgCl_2 \times 6H_2O$ were dissolved in PT.

1.1.4 Tris/EDTA 50 mmol/l tris, 50 mmol/l disodium ethylenediaminetetraacetate as aqueous solution adjusted to pH 7.2 with HCl.

1.1.5 AP Conjugate

The Behringwerke AG reagent called anti-bovine immunoglobulin-alkaline phosphatase conjugate and obtainable under product No. OUDY01 was diluted 1:70 with PT.

1.1.6 AP Substrate Solution 1.5 g/l p-nitrophenyl phosphate in 100 g/l diethanolamine in water adjusted to pH 9.5 with HCl.

1.2 Coating of Microassay Plates with Bovine Herpesvirus I (BHVI)

The microassay plates used were Immunoplates II 96 F with round bottoms (from Nunc, Roskilde, Denmark, article No. 262162). Tissue cultures of Madin-Darby bovine kidney cells (MDBK cells) in which BHVI had been grown, and tissue cultures which contained no BHVI, were processed, as described by Nicolai-Scholten et al. for mumps virus in Ned. Microbiol. Immunol. 168, 81–90, 1980, to give preparations which are called BHVI antigen (Ag) and (negative) control antigen (coAg) hereinafter. For the coating, 50 µl of BHVI antigen (Ag) and of coAg were placed alternately in the wells of the abovementioned microassay plates, and the plates were left to stand at 20–25° C. for 20 h. The contents of the wells were subsequently removed by aspiration, and the wells were washed once with PBS-Tween 20® and twice with tris/EDTA by filling and subsequent aspiration.

1.3 Method for Determination of IgM, IgG Antibodies Directed Against the Agents Causing IBR/IPV Positive control sera were diluted in serial dilution from 1:40 to 1:640 with the buffers PT and PT-Mg. Serum samples were diluted 1:44 with the above-mentioned buffers. 150 µl of each dilution were placed in wells of a microassay plate coated with Ag and coAg. The assay plate was then maintained at 37° C. with saturated atmospheric humidity for 1 h. The wells were subsequently washed three times with PBS-Tween® by filling the wells and aspirating out the liquid. Then 50 µl of AP conjugate were added, and the plates were again left to stand at 37° C. for 1 h and subsequently washed as described above. To determine the activity of the AP bound as conjugate in the wells, 100 µl of AP substrate solution were added, the microassay plate was left to stand at 37° C. for 45 min, and the extinction at 405 nm of the yellow-colored solutions was measured with an empty well as reference.

The sera were assessed as positive when the difference between the extinctions for the colored solutions in wells coated with Ag and for solutions in wells coated with coAg was greater than plus 200 milliextinctions (mE) and assessed as negative when the difference was less than plus 200 mE or was negative. The titer of a control serum was taken as the dilution at which this difference was less than 200 mE. The figure of 200 mE is therefore called the cutoff.

1.4 Result

The result of the measurement is shown in the table. It is evident from this that the addition of $MgCl_2$ to the sample dilution buffer PT causes no differences in the extinctions in the case of the two control sera diluted 1:640, either in the wells coated with Ag or in those coated with coAg. However, in the case of the sera diluted 1:44, the addition of $MgCl_2$ is advantageous inasmuch as the absolute figures for the extinctions both for the wells coated with Ag and for those coated with coAg are lower than the absolute figures for the extinctions when the buffer without the said additives is used. The reduction in the extinctions, especially in the wells coated with coAg, means that the background extinctions have been diminished and thus the specificity of the assay has been increased.

Example 2

ELISA for Detecting Antibodies Against the Agent Causing Bovine Leukosis 2.1 Buffer Solutions The following sample dilution buffers were prepared.

2.1.1 STD 10 ml/l fetal calf serum, 18 mmol/l trisodium citrate× $2H_2O$, 10 mmol/l KCl, 40 g/l 1-alkyl($C_8$ to $C_{18}$)amino-3-dimethylaminopropane 3-N-oxide in aqueous solution.

2.1.2 STD-Mg 50 mmol/l $MgCl_2$, i.e. 10 g/l $MgCl_2 \times 6H_2O$, were dissolved in the sample dilution buffer described in 2.1.1.

2.1.3 STD-Ca 68 mmol/l $CaCl_2$, i.e. 10 g/l $CaCl_2 \times 2H_2O$, were dissolved in the sample dilution buffer described in 2.1.1.

2.2. Coating of Microassay Plates with Bovine Leukemia Virus (BLV)

The microassay plates were the same as used in Example 1.2. BLV was grown on a permanent fetal sheep kidney cell line and processed to give preparations of BLV antigen as described for mumps virus by Nicolai-Scholten et al. in Med. Microbiol. Immunol. 168, 81–90, 1980. For the coating, 50 µl of BLV antigen were placed in each of the wells. No coating with a preparation of virus-free sheep kidney cells was carried out. Subsequently, the contents of the wells were removed by aspiration and the wells were washed once with PBS-Tween® and twice with tris/EDTA by filling and subsequent aspiration.

2.3 Method for the Determination of IgM and IgG Antibodies Directed Against BLV.

1:20 dilutions of BLV-positive bovine sera were prepared with the buffers STD, STD-$MgCl_2$ and STD-$CaCl_2$. 150 µl of these dilutions were pipetted into the wells, coated with BLV antigen, of the microassay plate described in Example 2.2. The microassay plate was further treated as described in Example 1.3.

2.4 Result

It emerged that the two analyte-negative sera produced an extinction of 0.46 E and 0.48 E respectively in STD. In STD-Mg and STD-Ca, this figure was reduced to 0.14 E and 0.22 E respectively, i.e. by 69.6% and 54.2% respectively. By contrast, the extinction reached by a bovine serum which contains BLV-specific antibodies was 1.28 E in STD, 1.06 E in STD-Mg, 1.02 E in STD-Ca; thus, the figure reached in STD was in this case reduced by only 17.2% and 20.3% respectively.

When the results are considered in conjunction, it is evident that the difference between the extinctions for analyte-positive and -negative sera becomes greater under the influence of $MgCl_2$ and $CaCl_2$ in the sample dilution medium, i.e. the specificity of the assay system is definitely improved.

TABLE

| | Sample dilution buffer | | | |
|---|---|---|---|---|
| | PT | | PT-Mg | |
| | $OD_{Ag}$ (mE) | $OD_{coAg}$ (mE) | $OD_{Ag}$ (mE) | $OD_{coAg}$ (mE) |
| IBR/IPV control serum, pos., (dilution 1:640) | | | | |
| Batch 16 32 08 | 181 | 43 | 172 | 45 |
| Batch 16 32 09 | 124 | 36 | 119 | 43 |
| Negative bovine sera (dilution 1:44) | 559 | 517 | 333 | 365 |
| | 472 | 485 | 324 | 262 |
| | 432 | 429 | 309 | 348 |
| | 703 | 722 | 529 | 537 |
| | 681 | 713 | 395 | 452 |
| | 198 | 161 | 142 | 97 |
| | 333 | 256 | 184 | 152 |
| | 861 | 867 | 675 | 674 |
| | 581 | 636 | 474 | 470 |
| | 493 | 503 | 374 | 387 |
| | 450 | 496 | 357 | 397 |
| | 768 | 819 | 501 | 583 |
| | 311 | 274 | 226 | 176 |
| | 893 | 978 | 758 | 781 |

What is claimed is:

1. A method for the immunochemical determination of an immunochemical reactive analyte in a biological material, comprising the steps of:

(a) preparing
  (i) a liquid phase comprising said biological material containing said reactive analyte, and a cation selected from the group consisting of calcium, magnesium, and a combination thereof, said cation being present in a concentration within the range of 30 to 100 mmol/l, and
  (ii) a solid phase having immobilized thereon a specific binding partner to said analyte, with the proviso that the solid phase is other than latex particles;

(b) contacting the liquid phase and the solid phase;

(c) separating the liquid phase and the solid phase; and (d) determining the extent of said reactive analyte binding to said specific binding partner.

2. The method of claim 1 wherein said cation is in the form of a salt and is selected from the group consisting of calcium chloride, magnesium chloride, and a combination thereof.

3. The method of claim 1, wherein said solid phase is an absorbent matrix.

4. The method of claim 1 wherein said specific binding partner is an antibody.

5. The method of claim 1, wherein the addition of said cations in the liquid phase of step (a) improves the specificity of the immunochemical reaction.

* * * * *